(12) United States Patent
Dufresne

(10) Patent No.: US 10,815,516 B2
(45) Date of Patent: Oct. 27, 2020

(54) METHOD FOR ESTABLISHING RESISTANCE CHARACTERISTICS OF A BIOLOGICAL INDICATOR

(71) Applicant: TSO3 Inc., Quebec (CA)

(72) Inventor: Sylvie Dufresne, Quebec (CA)

(73) Assignee: TSO3 Inc., Quebec (CA)

(*) Notice: Subject to any disclaimer, the term of this patent is extended or adjusted under 35 U.S.C. 154(b) by 29 days.

(21) Appl. No.: 14/955,452

(22) Filed: Dec. 1, 2015

(65) Prior Publication Data

US 2016/0160261 A1    Jun. 9, 2016

Related U.S. Application Data

(60) Provisional application No. 62/086,892, filed on Dec. 3, 2014.

(51) Int. Cl.
*G01N 33/48*   (2006.01)
*C12Q 1/22*    (2006.01)
*G06G 7/58*    (2006.01)

(52) U.S. Cl.
CPC ...................................... *C12Q 1/22* (2013.01)

(58) Field of Classification Search
None
See application file for complete search history.

(56) References Cited

U.S. PATENT DOCUMENTS

| | | | |
|---|---|---|---|
| 4,843,867 A | 7/1989 | Cummings | |
| 6,015,706 A | 1/2000 | Kim et al. | |
| 8,431,077 B2 * | 4/2013 | Goncalves | A61L 2/208 422/28 |

FOREIGN PATENT DOCUMENTS

| | | |
|---|---|---|
| CA | 2808897 A1 | 4/2011 |
| JP | H02502943 A | 9/1990 |
| JP | H10234360 A | 9/1998 |
| WO | 8906140 A1 | 7/1989 |
| WO | 2011038487 A1 | 4/2011 |

OTHER PUBLICATIONS

International Application No. PCT/CA2015/051252, IRS/WO dated Jan. 27, 2016.
Pflug, "Temperature Coefficient of Mircobial Destruction", Chapter 9, Microbiology and Engineering of Sterilization Processes; Tenth Edition; Minneapolis, Environmental Sterilization Laboratory, Aug. 28, 1999, pp. 20 pages.
Boscariol et al., "Sterilization by Pure Oxygen Plasma and by Oxygen-Hydrogen Peroxide Plasma: An Efficacy Study," International Journal of Pharmaceutics, 2008, vol. 353 (1-2), pp. 170-175.
Cebrian et al., "Role of the Alternative Sigma Factor [Sigma] B on *Staphylococcus aureus* Resistance to Stresses of Relevance to Food Preservation," Journal of Applied Microbiology, Jul. 2009, vol. 107 (1), pp. 187-196.
European Patent Application No. 15865809.6, Extended European Search Report dated May 14, 2018.
Ramaswamy et al., "Screening of Twelve Clostridium Botulinum (Group I) Spores for High-Pressure Resistance at Elevated-Temperatures," Food and Bioproducts Processing, Oct. 2013, vol. 91 (4), pp. 403-412.
Ramaswamy et al., "High-Pressure Destruction Kinetics of Clostridium Sporogenes ATCC 11437 Spores in Milk at Elevated Quasi-Isothermal Conditions," Journal of Food Engineering, Jan. 2010, vol. 96 (2), pp. 249-257.
English language abstract for JPH 02-502943 extracted from espacenet.com database on Nov. 6, 2019, 1 page (original document unavailable—see English language equivalent U.S. Pat. No. 4,843,867).
English language abstract for JPH 10-234360 extracted from espacenet.com database on Nov. 6, 2019, 1 page.

* cited by examiner

*Primary Examiner* — Eric S DeJong
(74) *Attorney, Agent, or Firm* — Howard & Howard Attorneys PLLC

(57) ABSTRACT

A method is provided for establishing resistance characteristics of a biological indicator in a sterilization process using a sterilant vapor. The method includes the step of creating a biological indicator inactivation profile by obtaining differential sterilant vapor pressure values in a sterilization chamber during sterilant vapor injection and determining D-values as a function of the differential sterilant vapor pressure values obtained. The biological indicator inactivation profile, when represented as a function of differential sterilant vapor pressure, may be linear over the full range of inactivation. The biological indicator inactivation profile may be created by injecting the sterilant vapor into the sterilization chamber and measuring biological indicator survival at different differential sterilant vapor pressure values. The method may include providing biological indicator inactivation data during sterilization at a given sterilization chamber temperature and initial sterilant concentration for use in creating the biological indicator inactivation profile at another temperature and sterilant concentration.

7 Claims, 4 Drawing Sheets

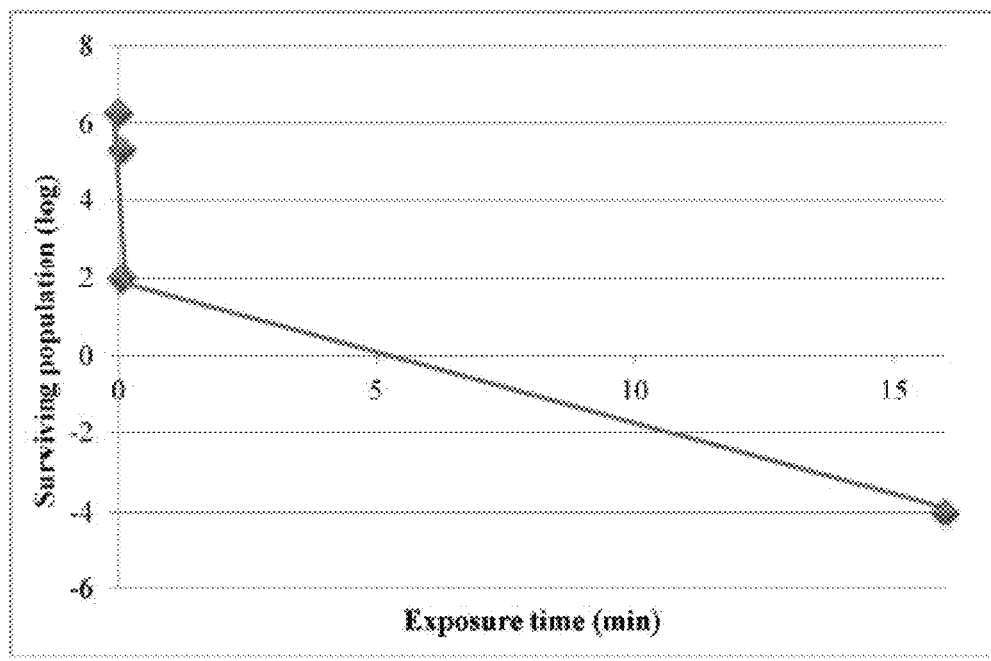
Figure 1 (PRIOR ART): Theoretical inactivation profile for a Manufacturer A BI over time
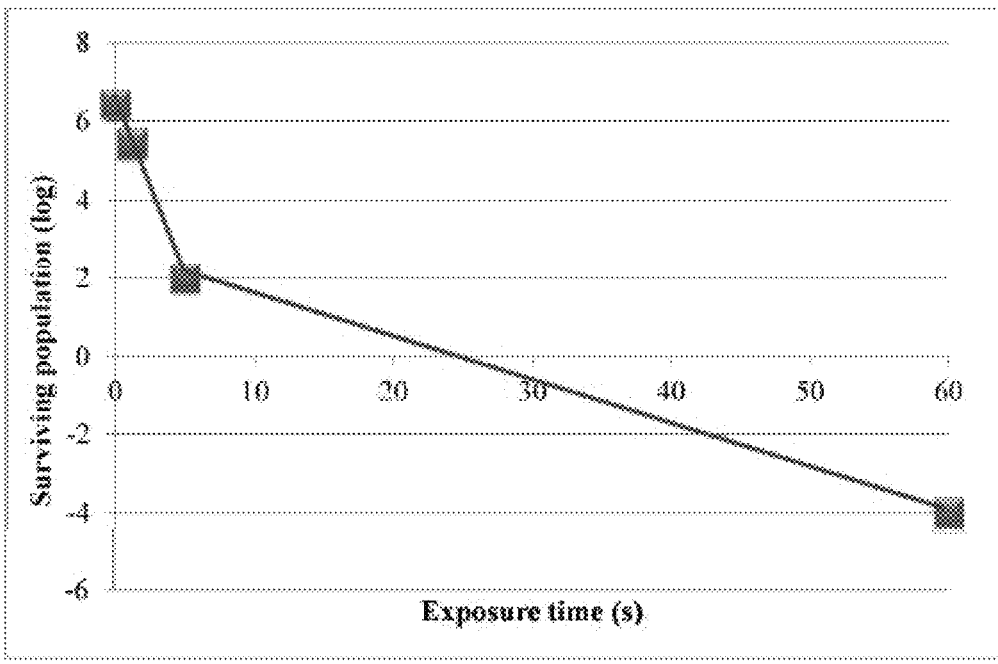
Figure 2 (PRIOR ART): Theoretical inactivation profile for a Manufacturer B BI over time

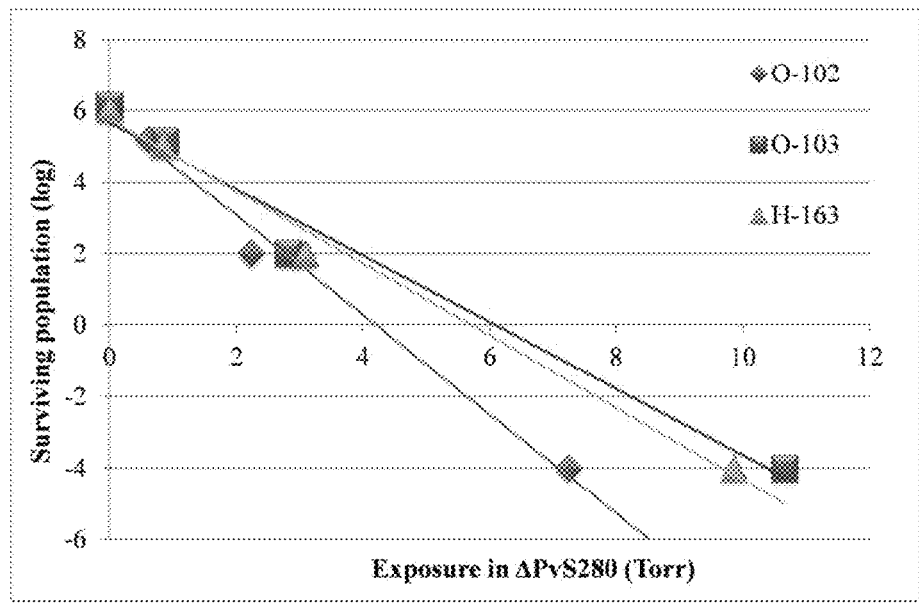
Figure 3: Theoretical inactivation profile for three lots of STERIZONE® BI+ biological indicator as a function of $\Delta Pv_{S280}$
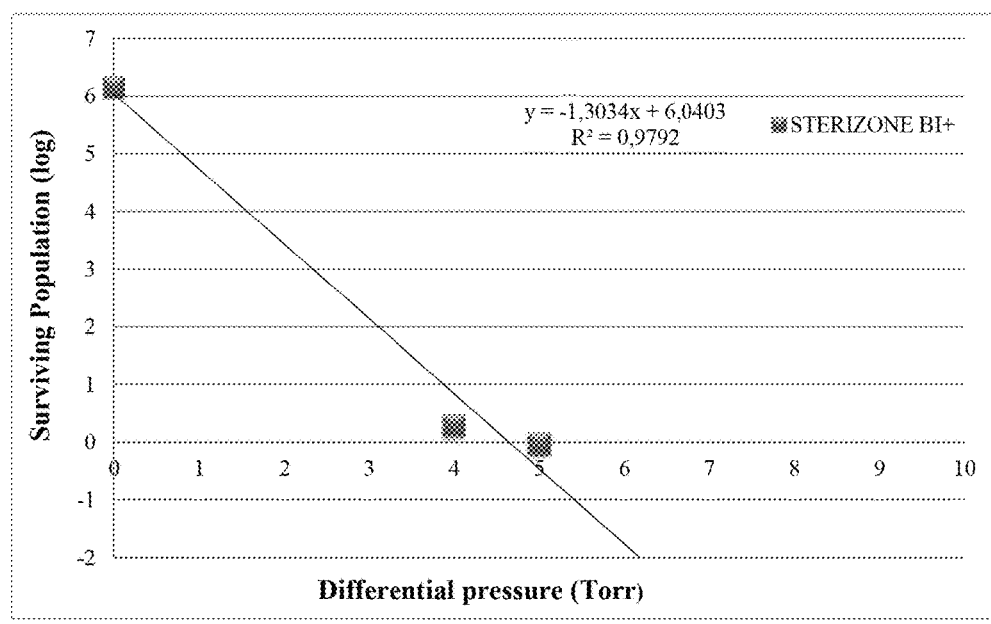
Figure 4: Experimental inactivation profile for a STERIZONE® BI+ as a function of $\Delta Pv_{S280}$ Figure 5: Experimental inactivation profile for a Manufacturer A BI as a function of $\Delta Pv_{S280}$ Figure 6: Experimental inactivation profile for a Manufacturer B BI as a function of $\Delta Pv_{S280}$

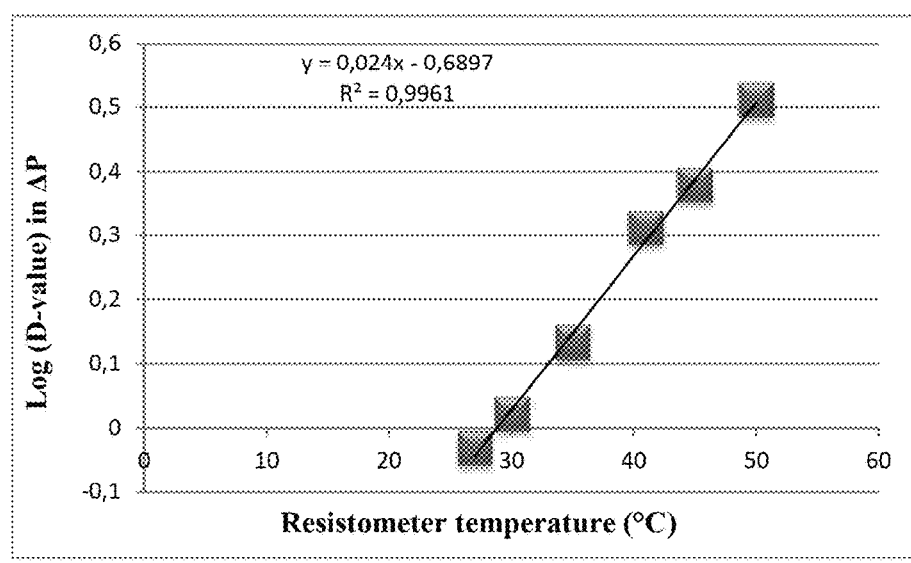
Figure 7: Experimental graph of the logarithm of the D-value as a function of the resistometer temperature

METHOD FOR ESTABLISHING RESISTANCE CHARACTERISTICS OF A BIOLOGICAL INDICATOR

This application claims the benefit of priority of U.S. Provisional Patent Application No. 62/086,892 filed Dec. 3, 2014, which is hereby incorporated by reference.

FIELD OF THE INVENTION

The present invention generally relates to indicator systems for determining the effectiveness of a sterilization process and more particularly relates to methods for establishing resistance characteristics of a biological indicator.

BACKGROUND OF THE INVENTION

In health care, as well as many other industries, it is nearly always necessary to monitor the effectiveness of processes used to sterilize equipment such as medical devices, waste materials, instruments and other disposable or non-disposable articles. In these settings, sterilization is generally defined as the process of completely destroying all viable microorganisms including structures such as infectious viruses, spores, fungus, etc. The standard practice in hospitals is to include a biological indicator (sterility indicator) in a batch of articles to be sterilized (usually called a load). The use of biological indicators (BIs) allows a direct and sensitive approach to assay the lethality of the sterilization process.

A standard type of biological indicator (BI) includes a known quantity of test microbial spores. This biological indicator is placed into the sterilization chamber and exposed to the sterilization process along with the objects to be sterilized. The test microbial spores, for example *Geobacillus stearothermophilus* or *Bacillus athrophaeus* spores, are incubated for a specified period of time under conditions which favor proliferation. The incubated BIs are then examined for indications of possible growth, such as for example the presence or absence of certain metabolic products, a pH change or the presence of turbidity produced by any surviving microorganisms. Positive growth, indicating the presence of viable spores, indicates that the sterilization process was insufficient to destroy all of the microorganisms.

There are international standards such as those defined by the International Organization for Standardization (ISO) that deal with sterilization. International standards dealing with the requirement for biological indicators are found in the ISO 11138 series.

ISO 11138-1 presents the general requirements defined for biological indicators used in Sterilization of health care products for various sterilization processes. Additional guidelines or requirements for specific sterilization processes are presented in ISO 11138-2, ISO 11138-3, ISO 11138-4 and ISO 11138-5 for ethylene oxide sterilization processes, moist heat sterilization processes, dry heat sterilization processes and low-temperature steam and formaldehyde sterilization processes respectively.

Hydrogen peroxide sterilization processes have become widely used since the 1990's. However, there are still no specific additional guidelines or requirements that have been defined for biological indicators used in hydrogen peroxide processes (or processes using similar sterilants such as peracetic acid or chlorine dioxide). Thus, biological indicators for hydrogen peroxide sterilization processes are generally evaluated only according to the general requirements of ISO-11138-1. That is not optimal, as will be apparent below.

Section 6.4.3 of ISO-11138-1 states that "Ideally, the survivor curve is linear over the full range of inactivation. In practice, deviations from this ideal occur, but linearity must be maintained within acceptable limits".

Section 6.4.4 states that "The survivor curve, when plotted as a semi-logarithmic curve of the log 10 of the viable test organism count against time, shall be linear with a correlation coefficient of at least 0.8."

BI evaluation resistometer (BIER) vessels have been used for more than 50 years to measure the resistance of bacterial spores when monitoring sterilization processes, mostly steam-sterilization processes. The earliest designs of steam-BIER vessels were developed by food-processing technologists, and were based on the concept of retorts used in the food-processing industry. BI resistometers exist for various sterilization processes using vaporized sterilants (ethylene oxide, formaldehyde), but not for vaporized hydrogen peroxide.

The lethality profile of a biological indicator for vaporized hydrogen peroxide sterilization processes (also called a VH2O2 BI) is usually defined using exposure times according to the general specifications provided in ISO 11138-1. However, as there are no standard conditions for a VH2O2 BI resistometer, every manufacturer of a VH2O2 BI currently uses their own specific exposure conditions, which results in the VH2O2 BIs of different manufacturers having different, non-standard performance data. For example, the exposure conditions of two manufacturers' existing products, referred to herein as Manufacturer A and Manufacturer B are as follows:

Manufacturer A: 2.7 mg/L VH2O2 at 50° C.;
Manufacturer B: 2.5 mg/L VH2O2 at 50° C.

The specific performance of a BI is assessed using the performance data of D-value, survival time and kill time, all of which are dependent on the exposure conditions respectively used. The D-value is a measure of resistance of the BI. According to ANSI/AAMI/ISO 11138-1, the D-value is defined as the time or dose (exposure conditions) required to achieve the inactivation of 90 percent of a population of the test microorganism under the stated exposure conditions. Thus, the D-value represents the exposure conditions required to achieve a 1-log reduction in active spores (with an initial population of at least $10^6$ active bacterial spores). For example, in a BI for a steam sterilization process with a D-value of 2 min at 121° C. (250 F) and a starting population of $10^6$ spores, 90% of the spores will be killed in the first 2 minutes of the cycle. In the next 2 min, 90% of the remainder will be killed, and so on. Thus, the kill rate progresses in a logarithmic manner, which results in a linear survivor curve when a logarithmic representation is used.

The survival time is the time required, at the exposure conditions used, to achieve at least a 4-log reduction, as shown in equation 1. The kill time is the time required, at the exposure conditions used, to achieve at least a 10-log reduction, as shown in equation 2, if the initial population is at least $10^6$ active bacterial spores.

$$\text{Survival time} \geq (\log 10 \text{ of initial population} - 2) \times D\text{-value} \quad (1)$$

$$\text{Kill time} \leq (\log 10 \text{ of the initial population} + 4) \times D\text{-value} \quad (2)$$

The performance data obtained with the BIs of Manufacturer A and Manufacturer B respectively are detailed below in Table 1.

Commercially available biological indicators are generally sold with a certificate of performance specific for each batch manufactured. The inactivation profile of the commercially available biological indicators for hydrogen peroxide may be estimated using the information provided by the values in this certificate of performance. In addition, the theoretical surviving population after a 1-log inactivation, the survival and kill times presented in Table 1 below, were obtained from the certificate of performance values provided by the manufacturers for each BI. Survival time and kill time were calculated according to equations 1 and 2, using the initial populations identified on the respective certificate of performance.

TABLE 1

Performance data and theoretical surviving population count for one lot of BI from two different manufacturers

| Performance criteria | BI Manufacturer A | | BI Manufacturer B | |
| --- | --- | --- | --- | --- |
| | Performance data value | Surviving population (log) | Performance data value | Surviving population (log) |
| Population | $2.0 \times 10^6$ (CFU) | 6.30 | $2.7 \times 10^6$ (CFU) | 6.43 |
| D-value | 4.1 seconds | 5.30 (−1 log) | 1.22 seconds | 5.43 (−1 log) |
| Survival time* | 4.0 seconds | 2.00 (−4.30 log) | 5.0 seconds | 2.00 (−4.43 log) |
| Kill time** | 16 minutes | −4.00 (−10.30 log) | 60 seconds | −4.00 (−10.43 log) |

*Sample calculation of the number of logs of inactivation using equation 1: 6.30 − 2 = 4.30 log
**Sample calculation of the number of logs of inactivation using equation 2: 6.30 + 4 = 10.30 log Values found in Table 1 were transferred mathematically to graphs to define the theoretical lethality profile of each biological indicator (BIA; BIB). As is apparent from the graphical representations in FIGS. 1 and 2, the inactivation profile of these biological indicators is biphasic as a function of the exposure time of the testing conditions used.

Since the inactivation profile of these types of biological indicators is not linear as a function of exposure time over the full range of inactivation, the sterility assurance level potential of the sterilization process cannot be accurately predicted using these BIs.

Moreover, since every hydrogen peroxide manufacturer is using different conditions of hydrogen peroxide concentration or dose, or testing chamber temperature, it is very hard to define common parameters to compare the resistance/performance characteristics of different hydrogen peroxide biological indicators.

At current, no known VH2O2 BI exists that will provide a linear inactivation profile over the full range of inactivation as a function of the exposure time of the testing conditions used.

It would therefore be desirable to provide an improved method or process that would reduce at least one of the above mentioned drawbacks of known methods for estimating resistance or performance characteristics of a biological indicator in a sterilization process or for evaluating the effectiveness of a sterilization process, for instance a hydrogen peroxide process.

SUMMARY

It is an object of the present invention to obviate or mitigate at least one disadvantage of previous methods for establishing resistance characteristics of a biological indicator in a sterilization process, or for evaluating the effectiveness of a sterilization process.

Accordingly, there is provided a method for establishing resistance characteristics of a biological indicator in a sterilization process using a sterilant vapor. The method comprises the steps of creating a biological indicator inactivation profile by obtaining differential sterilant vapor pressure values in a sterilization chamber during sterilant vapor injection and determining D-values as a function the differential sterilant vapor pressure values obtained.

In one embodiment, the biological indicator inactivation profile is created by gradually injecting the sterilant vapor into the sterilization chamber and measuring biological indicator survival at different differential sterilant vapor pressures determined at different times of the sterilant vapor injection. Preferably, the injection of the sterilant vapor is pulsed for the generation of a layer of micro-condensation of the sterilant in the chamber.

In another embodiment, the method may further comprise providing biological indicator inactivation data during sterilization at a given sterilization chamber temperature and an initial sterilant concentration for use in creating the biological indicator inactivation profile at another sterilization chamber temperature and sterilant concentration.

In a further embodiment, the method may further comprise evaluating the biological indicator inactivation profile against a standard to evaluate the effectiveness of the biological indicator in testing a sterilization process.

In still a further embodiment, the sterilant vapor is hydrogen peroxide vapor.

The method may also provide more accurate resistance characteristics for any biological indicator.

Moreover, the method may provide a linear inactivation profile of a biological indicator over the full range of inactivation.

According to another aspect, there is also provided a method for evaluating the effectiveness of a sterilization process. The method comprises the steps of carrying out the sterilization process using the biological indicator as defined herein, measuring biological indicator survival at different differential sterilant vapor pressures; and evaluating the measured biological indicator survival against the biological indicator inactivation profile for evaluating the effectiveness of the sterilization process.

According to a further aspect, there is also provided a biological indicator or commercial package including the biological indicator wherein the resistance characteristics are as established herein. The resistance characteristics may be first defined in differential pressure and expressed in equivalent time or dose parameters. The inactivation profile may be linear over a full range of inactivation. The biological indicator or commercial package may have a coefficient of determination ($r^2$) for the lethality profile (linearity) of at least 0.8 using at least 3 points.

According to yet a further aspect, the biological indicator or commercial package may be used for monitoring a sterilization process.

According to still a further aspect, a biological indicator and the resistance characteristics thereof established according to the method of the invention may be used for evaluating the effectiveness of a sterilization process.

In one embodiment, there is provided a method for establishing resistance characteristics of a biological indicator submitted to a sterilization process, including the steps of subjecting the biological indicator to a gradually and continuously increasing sterilant vapor pressure in a sterilization chamber to create a micro-layer of condensed sterilant on the load to be sterilized; measuring differential pressures of sterilant vapor during the subjecting step; determining a D-value as a function of the differential pressures of sterilant vapor reached; calculating surviving population data with the determined D-value wherein said surviving population data, when plotted as a semi logarithmic curve of the log 10 of the viable test organism count against the differential pressure, provide a predictable linear inactivation profile.

In another embodiment, a relationship may be determined between the D-value obtained from different testing chamber temperatures.

The inactivation profile may be linear over a range of testing chamber temperatures. Thus, as for steam sterilization processes, a D-value can be defined at each required testing chamber temperature. In addition, a relationship similar to the z-value defined for steam exists also for hydrogen peroxide biological indicator using this method.

BRIEF DESCRIPTION OF THE DRAWINGS

In order that the invention may be readily understood, embodiments of the invention are illustrated by way of example in the accompanying drawings.

FIG. 1 (PRIOR ART) is a graphical representation of a theoretical inactivation profile for a Manufacturer A BI (biological indicator) over time.

FIG. 2 (PRIOR ART) is a graphical representation of a theoretical inactivation profile for a Manufacturer B BI (biological indicator) over time.

FIG. 3 is a graphical representation of a theoretical inactivation profile for three lots of STERIZONE® BI+ biological indicator as a function of ΔPvS280, according to one embodiment of the invention.

FIG. 4 is a graphical representation of an experimental inactivation profile for a STERIZONE® BI+ as a function of ΔPvS280, according to one embodiment of the invention, when tested in the $TSO_3$ resistometer.

FIG. 5 is a graphical representation of an experimental inactivation profile for Manufacturer A BI as a function of ΔPvS280, according to one embodiment of the invention when tested in the $TSO_3$ resistometer.

FIG. 6 is a graphical representation of an experimental inactivation profile for Manufacturer B BI as a function of ΔPvS280, according to one embodiment of the invention when tested in the $TSO_3$ resistometer.

FIG. 7 is an experimental graph of the logarithm of the D-value as a function of the $TSO_3$ resistometer temperature.

Further details of the invention and its advantages will be apparent from the detailed description included below.

DETAILED DESCRIPTION

In the following description of the exemplary embodiments, references to the accompanying drawings are by way of illustration of examples by which the invention may be practiced. It will be understood that other embodiments may be made without departing from the scope of the invention disclosed.

The term "sterilization" generally refers to rendering a substance incapable of reproduction, metabolism and/or growth. While this is often taken to mean total absence of living organisms, the term may be used herein to also refer to a substance free from living organisms to a target degree previously agreed to be acceptable. Thus, unless otherwise indicated, the term sterilization may be used herein to also refer to methods and procedures less rigorous than sterilization, for example, decontamination and the like. Moreover, although the methods of the invention will be described herein in the particular field of sterilization of medical devices, the skilled addressee will appreciate that other applications may be envisaged, for example various commercial and industrial applications.

In this specification, the term sterilization chamber under vacuum refers to a previously evacuated chamber which has been sealed except for admission of the sterilant vapor.

In this specification, the term differential sterilant vapor pressure refers to the vapor pressure existing in a previously evacuated sterilization chamber at different times during gradual injection of sterilant vapor into the chamber. Gradual injection in this context refers to continuous injection of an amount of sterilant vapor that is smaller and may be significantly smaller than the total amount of sterilant expected to be necessary for sterilization (expected amount). Gradual injection may also mean pulsed injection of aliquots of sterilant vapor which are only a fraction of the expected amount. For example, the amount may be 1/15th of the expected amount, or less and the aliquots may each be 1/5th of the expected amount or less. To verify lethality, measurements may be taken, for example, at pressure fractions which are about 1/15 of the final differential pressure reach. For example, the number of positive BIs may be verified after 1.25 Torr, 2.5 Torr, 3.75 Torr, etc. are reached. The BI may be completely inactivated after a pressure differential of as little as 6 Torr or up to 9 to 10 Torr at 23° C. The size of the pressure fractions used and the min-max size of the pressure fractions may be chosen depending on the sterilization chamber temperature.

Throughout the present description, the invention will be described in relation to one particular exemplary embodiment wherein the biocide used for sterilization is vaporized hydrogen peroxide. In one embodiment, an aqueous solution of hydrogen peroxide, for instance a 50 wt % hydrogen peroxide solution such as the STERIZONE® 125-280 Solution™ available from $TSO_3$ Inc., Quebec, Canada, is used to generate the sterilant vapor. The skilled addressee will appreciate that other concentrations of the solution (3% to 59% for non-limitative examples) or other liquid biocides for evaporation may be envisaged for a specific application without departing from the scope of the invention.

Applicant is developing enhanced hydrogen peroxide sterilization processes and systems particularly designed for sterilization of general instruments, single or multiple channels flexible endoscopes and rigid channeled devices including single channel and double channel rigid endoscopes for example, the effectiveness of such processes having to be ascertained through the use of biological indicators, as detailed above. One exemplary embodiment of such system is the STERIZONE® VP4 Sterilizer (subsequent version of formerly known STERIZONE® 125L+ Sterilizer) available from $TSO_3$ Inc., as described in published international patent application no. WO2011/038487 from the same applicant, such application being incorporated by reference herein in its entirety.

In order to ascertain the effectiveness of a given sterilization process in a specific sterilization system (i.e. defining resistance characteristics of biological indicators and chemical indicators), a resistometer whose test conditions are consistent with conditions found in the commercial sterilizer devised for health care facilities has to be used, according to ANSI/AAMI/ISO 18472 standard.

In one embodiment, the sterilizer/resistometer used to implement the sterilization processes, in this specification also referred to as the TSO3 resistometer, has a 125 liters electropolished stainless steel sterilization chamber. Heating blankets covering the entire exterior surface of the chamber are used to maintain the chamber wall temperature at a predetermined temperature, 41° C. in an exemplary embodiment. The sterilizer is equipped with a pressure sensor inside the sterilization chamber and additional instrumentation such as a balance to measure the mass of vaporized sterilant injected in the chamber and a data logger having a recording interval of one point per second for each of the measurement points. As detailed below, the sterilant injection is controlled using the same pressure sensor as for a standard production unit. The skilled addressee will thus appreciate that, under the same loading conditions, the reaction of a biological indicator in an actual sterilizer used in a health care facility would be similar to the reaction obtained in this resistometer unit.

In a second tested embodiment, the sterilizer/resistometer used to verify the impact of chamber temperature of the biological D-value has a 55 liters aluminum chamber. Heating blankets covering the exterior surface of the chamber were used to maintain the chamber wall temperature at a predetermined temperature. The resistometer/sterilizer is equipped with a pressure sensor inside the chamber and additional instrumentation such as a balance to measure the mass of vaporized sterilant injected in the chamber, a UV system and a data logger.

In one embodiment, the used sterilizer/resistometer uses vaporized hydrogen peroxide ($H_2O_2$) as the sterilant, either used alone or in combination with a subsequent injection of ozone, as described in previously mentioned international patent application no. WO2011/038487. The sterilizer embeds a Dynamic Sterilant Delivery System™ which provides an exposure to the vaporized hydrogen peroxide at a gradually increasing sterilant vapor pressure through multiple small pulsed injections of the hydrogen peroxide sterilant into the chamber previously evacuated. Measuring the sterilant vapor pressure in the chamber allows for the determination of a differential sterilant vapor pressure in the chamber after each injection pulse.

For testing, the biological indicators are loaded into the sterilization chamber and the door is closed. The chamber is initially subjected to a vacuum of 1 Torr, referred to as preconditioning step. Then, the exposure to hydrogen peroxide begins with the Dynamic $H_2O_2$ exposure step. During this step, a 50%/wt hydrogen peroxide solution, referred to as 125-280 Solution™ (available from $TSO_3$ Inc.), is gradually injected in vapor form into the sterilization chamber until a differential pressure is reached in the chamber. The differential pressure chosen will vary as a function of the desired lethality (BI inactivation) to be achieved. The ISO 11138-1 standard is requiring at least 5 different exposure points to calculate a D-value.

Once the differential pressure is reached, there is no additional exposure and no ozone injection. The chamber is immediately subjected to a vacuum of 1 Torr, resulting in the removal of the chemical components from the chamber. Ventilation to the atmosphere with filtered ambient air or high purity dry medical grade oxygen (93%) is performed, at which point the chamber door can be safely opened.

The biological indicators are then retrieved and incubated in accordance with the manufacturer instruction to determine whether or not they are sterile.

During the Dynamic $H_2O_2$ exposure step, the contents of the chamber are exposed to vaporized hydrogen peroxide, using the $H_2O_2$ solution composed of 50 wt % $H_2O_2$. The $H_2O_2$ solution is drawn out of a bottle by a vacuum and vaporized using a precise dual-valve vaporization system connected to a heated vaporizer, which is itself connected to the sterilization chamber, as detailed in previously mentioned international application no. WO2011/038487.

To be able to accurately control the vaporization rate and ensure a complete vaporization of the hydrogen peroxide solution, the interval between the opening of the two valves and the opening frequency of each of the two valves (controlling the time between vaporizations) is controlled by a programmable logic controller (PLC), which at the same time monitors the pressure inside the chamber and drives the vaporizer circuit board. The vaporization process is designed to establish a controlled evolution of vaporized hydrogen peroxide and water pressure inside the chamber up to the expected differential vapor pressure ($\Delta PvS280$) set point. The differential pressure is defined as the difference between the initial chamber pressure and the final chamber pressure during the Dynamic $H_2O_2$ exposure step.

In this described embodiment, the vaporizer has an aluminum block heated to 120° C. A set of two valves, up-stream of the vaporizer, controls the injection of the sterilant solution. The quantity of solution per pulse entering the vaporizer is approximately 40 mg, with approximately 1 pulse per second, in the case of a 125 liters chamber. The vaporized solution is drawn into the chamber by the vacuum. This sequence is repeated until the expected differential pressure $\Delta PvS280$ is reached.

The inventor of the present invention has discovered that, in low temperature sterilization processes similar to the exemplary embodiment described above, the differential pressure of vaporized solution injected ($\Delta PvS280$) is the critical process parameter that may be used to establish the resistance characteristics of the biological indicator.

Therefore, according to an embodiment of the present invention, the inactivation profile of the biological indicator used in such sterilization processes may be represented as a function of $\Delta PvS280$, instead of time, as in the current practice up to now.

The inventor of the present invention has further discovered that, when plotted as a semi-logarithmic curve of the log 10 of the viable test organism count against $\Delta PvS280$, the inactivation curve of the biological indicator is linear over the full range, with a correlation coefficient of at least 0.8. This is of particularly great advantage since it provides a method to establish and predict a linear inactivation profile of the biological indicator over its full range of inactivation.

One advantage of this method is that the equations of ISO 11138-1 for survival and kill exposure can be used to predict the experimental values, whereas the survival and kill value couldn't be predicted using the usual ISO 11138 and had to be defined experimentally by each biological indicator manufacturer. In addition, this method can be applied for different hydrogen peroxide solution concentrations and testing chamber temperatures.

Table 2 below shows performance data and theoretical surviving population counts of three lots of tested biological indicators, such suitable biological indicators will be discussed in more detail hereinafter. The tests shown in Table 2 were performed in the 125 liters electropolished stainless steel sterilization chamber TSO3 resistometer as described above. The performance data, i.e. average D-value, survival time and kill differential pressure are listed. As for Manufacturer A and Manufacturer B BIs discussed above, the theoretical surviving population after 1-log inactivation (D-value), the survival and kill parameters, were obtained for each performance criteria.

tivation profile of the two other tested biological indicators are each linear as a function of the differential pressure $\Delta PvS280$. Coefficients of determination ($r^2$) for both curves are greater than 0.8, as defined in ANSI/AAMI/ISO 11138-1 for a linear inactivation.

As should become apparent from a reading of the present description, the differential pressure of vaporized hydrogen peroxide solution injected is a good predictor of the microbial inactivation of a hydrogen peroxide sterilization process, and can be used to establish and/or predict a linear inactivation of self-contained biological indicators, which is of great advantage.

TABLE 2

Performance data and theoretical surviving population count of three different lots of tested BIs

| Performance criteria | Lot O-102 | | Lot O-103 | | Lot H-163 | |
|---|---|---|---|---|---|---|
| | Performance data value | Surviving population (log) | Performance data value | Surviving population (log) | Performance data value | Surviving population (log) |
| Population | 1.57 x 10$^6$ (CFU) | 6.20 | 1.43 x 10$^6$ (CFU) | 6.15 | 1.06 x 10$^6$ (CFU) | 6.06 |
| D-value | 0.61 Torr | 5.20 (−1 log) | 0.88 Torr | 5.15 (−1 log) | 0.84 Torr | 5.06 (−1 log) |
| Survival $\Delta Pv_{S280}$ | 2.23 Torr | 2.00 (−4.20 log) | 2.82 Torr | 2.00 (−4.15 log) | 3.03 Torr | 2.00 (−4.06 log) |
| Kill $\Delta Pv_{S280}$ | 7.24 Torr | −4.00 (−10.20 log) | 10.66 Torr | −4.00 (−10.15 log) | 9.86 Torr | −4.00 (−10.06 log) |

FIG. 3 shows the graphical representation of the theoretical inactivation kinetics profile for the three lots of biological indicators based on the D-value determined as a function of the differential vapor pressure $\Delta PvS280$. The survival and kill parameters defined using the ISO 11138-1 equations were experimentally confirmed. This confirms that the theoretical inactivation profile is linear when the differential pressure of vaporized sterilant solution injected is used for establishing the resistance characteristics.

An Example of a suitable biological indicator is the STERIZONE® BI+ Self-Contained Biological Indicator available from TSO$_3$ Inc. and manufactured for TSO$_3$, according to specifications defined in a private label agreement. The Self-contained Biological Indicator carrier is made of stainless steel and is compatible with the STERIZONE® sterilization process. Furthermore, it is inoculated with spores of G. stearothermophilus.

Experiments using the methodologies as detailed below, have been performed to experimentally study the lethality of the STERIZONE® BI+. The lethality study was performed under conditions representative of the dynamic H$_2$O$_2$ exposure step of the STERIZONE® sterilization process detailed above. The dynamic H$_2$O$_2$ exposure step is controlled by the differential pressure ($\Delta PvS280$) of vaporized sterilant solution injected into the sterilization chamber. As previously mentioned, the differential vapor pressure ($\Delta PvS280$) is the critical process parameter used to study the inactivation kinetics during the dynamic H$_2$O$_2$ exposure step of the sterilization cycle.

In this study, the resistance characteristics of the biological indicators of Manufacturers A and B were also analysed.

FIGS. 4, 5 and 6 respectively show the experimental inactivation profiles for the STERIZONE® BI+ and the Manufacturer A and Manufacturer B BIs expressed as a function of the differential pressure $\Delta PvS280$ tested in conditions representative of the resistometer and the STERIZONE® sterilization process conditions. As can be seen, the inactivation profile of the STERIZONE® BI+ and the inac- Methodology The fraction negative method was used to determine the D-value of all BIs. According to ANSI/AAMI/ISO 11138-1:2006(R)2010, a minimum of five different exposure conditions are required for D-value determination by the fraction negative method: Exposure conditions where all the indicators are positive; two successive exposure conditions where all the indicators are negative; and at least two exposure conditions in which a fraction of the samples shows growth.

For each exposure point, twenty BIs were placed on the shelf of the resistometer for each selected exposure condition. The BIs were exposed to incremental differential pressure set points ($\Delta PvS280$) during the dynamic H$_2$O$_2$ exposure step, as previously detailed.

After exposure and for each BI, BI medium were activated by placing the indicator in an upright position in a plastic crusher and by gently squeezing the crusher to break the glass ampoule holding the nutrient media. Then, the BIs were placed in the incubator and incubated according to each manufacturer's instructions for use.

The mean D-value "$\overline{D}$" was estimated using the Holcomb-Spearman-Karber procedure described in ANSI/AAMI/ISO 11138-1: 2006(R)2010, incorporated herein by reference, as shown in equation 1.

$$\overline{D} = \frac{U_{HSK}}{\text{Log}N_0 + 0.2507} \quad (1)$$

Where:
N$_0$ is the initial viable count of the test organisms per sample; and $$U_{HSK} = \Sigma_{i=1}^{k-1} U_i \text{ and } U_i = x_i y_i \quad (2)$$

However, according to an embodiment of the present invention, the time exposure to the sterilizing agent generally used in prior art for the calculation of $x_i$ and $y_i$ is replaced by differential pressure "$\Delta P$", as shown in equation 3.

$$x_i = \frac{\Delta P_i + \Delta P_{(i+1)}}{2} \quad (3)$$

$$y_i = \frac{r_{(i+1)}}{n_{(i+1)}} - \frac{r_i}{n_i} \quad (4)$$

Where:

$r_i$ is the number of samples showing no growth for an exposure to $\Delta P_i$ $n_i$ is the number of exposed sample at an exposure to $\Delta P_i$ The 95% confidence interval for the mean D-value $\overline{D}$ (p=0.05) "Dcalc" is calculated using equation 5:

$$D_{calc} = \overline{D} + 2\sqrt{V} \quad (5)$$

The variance "V" is calculated using equation 6:

$$V = a\left(\frac{2.3026}{\ln N_0 + 0.5772}\right)^2 \quad (6)$$

And "a" of the variance is calculated using equation 7:

$$a = 0.25 \sum_{i=2}^{i=6} \left\{ [\Delta P_{i+1} - \Delta P_{i-1}]^2 \left[ r_i \frac{n_i - r_i}{n_i^2(n_i - 1)} \right] \right\} \quad (7)$$

The differential pressure of the vaporized sterilant solution ($\Delta$PvS280) injected during the dynamic $H_2O_2$ exposure step of the cycle is the parameter set and monitored to achieve, from partial to complete, inactivation of the biological indicators for the fraction negative tests used to calculate the D-value. The results for the fraction negative tests performed for the STERIZONE® BI+ are presented in Table 3 below. In addition, the D-value was calculated in units of differential pressure $\Delta$PvS280 using the Holcomb-Spearman-Karber procedure as previously described.

TABLE 3

Data from Fraction Negative Method for the STERIZONE® BI+

| | STERIZONE® BI+ | |
|---|---|---|
| $n^1$ | $\Delta Pv_{S280}$ (Torr) | $r^2$ |
| 20 | — | — |
| 20 | 2.50 | 0 |
| 20 | 4.00 | 3 |
| 20 | 5.00 | 8 |
| 20 | 7.50 | 20 |
| 20 | 8.75 | 20 |
| D-value ($\Delta Pv_{S280}$) | 0.84 ± 0.07 | |

[1]Number of samples per test
[2]Number of sterile (negative) samples per test

In addition, the survival-kill parameters of the STERIZONE® BI+ were also defined according to the Survival-kill window determination. According to ISO 11138-1 previously mentioned, the survival and kill parameters were calculated using equations 8 and 9 below and are shown in Tables 4 and 5:

$$\text{Survival} = (\log No - 2) \times D\text{-value} \quad (8)$$

$$\text{Kill} = (\log No + 4) \times D\text{-value} \quad (9)$$

The D-value being defined using equation 1 above.

TABLE 4

Survival data in $\Delta P$ units

| Lot | $\Delta P$ (Torr) |
|---|---|
| STERIZONE® BI+ | 3.52 |

TABLE 5

Kill data in $\Delta P$ units

| Lot | $\Delta P$ (Torr) |
|---|---|
| STERIZONE® BI+ | 8.56 |

Although the Fraction Negative Method (based on the most probable number) has been detailed herein for use in carrying out the present invention, this method is not critical for the execution of the invention and other suitable alternative methods such as direct count may also be used without departing from the scope of the present invention.

As previously mentioned, the sterilization principle of the STERIZONE® sterilization process is based on the formation of a micro-layer of sterilant, i.e. hydrogen peroxide for example, on the load to be sterilized. The micro-layer formation is dependent on the saturation pressure of the sterilant solution, i.e. its initial concentration, and is also influenced by the temperature of the atmosphere inside the chamber.

The inventor of the present invention has further discovered that, in low temperature sterilization processes similar to the exemplary embodiment described above, a relationship exist between the D-value and the testing temperature of the resistometer or sterilizer chamber, as detailed below.

In fact, this type of relationship is known for steam sterilization processes and is called z-value. Pflug, in Microbiology and engineering of sterilization processes; Tenth edition; Minneapolis, Environmental Sterilization Laboratory. Pages 1 to 22.9 (1999), is defining the z-value as the degrees of temperature change for the straight line of a given inactivation profile to traverse one logarithmic cycle. It is also the degrees of temperature change ($\Delta T$) for the D-value to increase by a factor of ten. According to ANSI/AAMI/ISO 11138-1: 2006(R) 2010, it is defined as the change in exposure temperature of a thermal sterilization process, which corresponds to a tenfold change in D value.

To study the influence of temperature on the sterilization process, the D-value of the STERIZONE® BI+ lot O-103 was determined for the $TSO_3$ resistometer having a 55 liters aluminum chamber at a plurality of chamber wall temperatures, i.e. 27° C., 30° C., 35° C., 41° C., 45° C., and 50° C.

For each selected exposure condition, twenty STERIZONE® BI+ were placed in a BI support. The support was placed on the shelf of the resistometer. The load was exposed to incremental differential pressure set points ($\Delta Pv_{S280}$) during the dynamic $H_2O_2$ exposure, as previously described. Once the differential pressure was reached, it was followed by a ventilation step with a vacuum to 1 Torr without any exposure time and ozone injection, as detailed above.

The z-value determination was estimated using the method described in Annex B of ANSI/AAMI/ISO 11138-3: 2006, which is incorporated by reference herein, where the determining factor of time generally used in the prior art was replaced by the differential pressure "ΔP".

The log of the D-value calculated for each temperature was plotted against the exposure temperature in degrees Celsius. The z-value is equal to the slope of the best-fit rectilinear curve as determined by the regression analysis as shown in equation 10.

$$z\text{-value} = 1/m \text{ where } m \text{ is the slope} \tag{10}$$

Results for the performed fraction negative tests (D-value) for each tested temperature are presented in Table 6. In addition, the D-value was calculated in units of differential pressure ΔP using the Holcomb-Spearman-Karber procedure as previously described.

shown with the linear regression with a correlation coefficient of 0.99. The z-value was calculated to be 42° C. for the STERIZONE® BI lot O-103. This means that an increase in the resistometer temperature of 42° C. will cause a tenfold increase of the D-value.

Once the D-value in ΔP is calculated, it can be expressed in units of exposure time or dose using the relationship existing between the differential pressure of vaporized solution injected and the injection time or injected mass, as will be appreciated by the skilled addressee. Since this relationship is temperature dependent, it has to be defined for each temperature. The D-value expressed in time and injected sterilant dose are presented in Table 7.

TABLE 6

Data from Fraction Negative Method for different resistometer temperatures

| | 27° C. | | 30° C. | | 35° C. | | 41° C. | | 45° C. | | 50° C. | |
|---|---|---|---|---|---|---|---|---|---|---|---|---|
| n* | ΔP (Torr) | r** | ΔP (Torr) | r** | ΔP (Torr) | r** | ΔP (Torr) | r** | ΔP (Torr) | r** | ΔP (Torr) | r** |
| 20 | 4 | 0 | 5 | 0 | 6 | 0 | 5 | 0 | 13 | 0 | 10 | 0 |
| 20 | 5 | 1 | 6 | 8 | 8 | 7 | 7 | 1 | 15 | 10 | 15 | 1 |
| 20 | 6 | 11 | 7 | 11 | 10 | 16 | 10 | 0 | 17 | 19 | 20 | 8 |
| 20 | 7 | 19 | 8 | 17 | 12 | 20 | 13 | 7 | 19 | 18 | 25 | 18 |
| 20 | 8 | 20 | 9 | 20 | 14 | 20 | 15 | 18 | 21 | 19 | 30 | 20 |
| 20 | 10 | 20 | 10 | 20 | | | 17 | 19 | 23 | 20 | | |
| 20 | | | | | | | 19 | 20 | 23 | 20 | | |
| D-value | 0.93 ± 0.04 Torr | | 1.05 ± 0.06 Torr | | 1.36 ± 0.09 Torr | | 2.05 ± 0.11 Torr | | 2.39 ± 0.09 Torr | | 3.24 ± 0.22 Torr | |

*Number of samples per test
**Number of sterile (negative) samples per test

As known to the skilled addressee, with saturated steam, the higher the sterilization temperature, the shorter the time required to inactivate a biological indicator. The lethal agent of steam is heat, more precisely, a molecular energy state capable of producing changes in the cell. The temperature at which denaturation occurs varies inversely with the amount of water present. Sterilization in saturated steam thus requires precise control of time, temperature, and pressure.

As for any other vapor, the saturation pressure of water vapor increases as a function of the temperature. With hydrogen peroxide processes using a hydrogen peroxide solution of known concentration, the saturation pressure increases also as a function of the temperature. However, contrary to the D-value in steam processes, the D-value for hydrogen peroxide processes, when expressed in differential pressure, will increase with temperature. This is explained by the fact that the sterilizing agent is not the latent heat, as for steam, but in part due to the formation of a concentrated micro-layer of hydrogen peroxide on exposed surfaces. As shown in Table 6, the D-value at 50° C. (3.24 Torr) is higher compared to the D-value at 30° C. (1.05 Torr).

The D-values of the STERIZONE BI+ were established for six different temperatures of the resistometer. Then, the log of D-value calculated for each temperature was plotted against the exposure temperature in degrees Celsius, as shown in FIG. 7, to determine the regression equation and the correlation coefficient ($r^2$).

As shown in FIG. 7, a linear relationship is demonstrated between the D-value and the resistometer temperature as

TABLE 7

D-values expressed in ΔP, time and dose

| Resistomater temperature | D-value in units of $\Delta P v_{S280}$ (Torr) | D-value in units of exposure time (s) | D-value in units of $H_2O_2$ dose injected (mg/L) |
|---|---|---|---|
| 27° C. | 0.93 ± 0.04 | 3.6 | 1.15 |
| 41° C. | 2.05 ± 0.11 | 6.1 | 1.50 |
| 50° C. | 3.24 ± 0.22 | 7.9 | 2.02 |

As expected, the D-values expressed in ΔP, time and dose are all increasing as a function of the resistometer temperature.

As it should now be apparent to the skilled addressee upon reading of the present description, a relationship exists between the D-value and the temperature of the hydrogen peroxide resistometer when the D-values are defined using as the process control variable the differential pressure of vaporized hydrogen peroxide injected.

The skilled addressee will appreciate that embodiments of the present invention may be used to verify if the inactivation profile of a specific BI is linear when expressed as a function of the differential pressure of the solution injected. The skilled addressee will also appreciate that embodiments of the present invention may be used to better compare the resistance of various BIs exposed to the same sterilization conditions, which is of great advantage.

The skilled addressee will also appreciate that the method described herein may be used to evaluate and/or develop new BIs with selected resistance characteristics for a specific application and/or sterilization process.

In the preceding description, for purposes of explanation, numerous details are set forth in order to provide a thorough understanding of the embodiments of the invention. However, it will be apparent to one skilled in the art that these specific details are not required in order to practice the invention.

What is claimed is:

1. A method for identifying one or more biological indicators (BIs) suitable for a sterilization process, the method comprising:
   (1) (a) placing one or more BIs of a batch of BIs in a resistometer;
   (b) applying a vacuum to the resistometer;
   (c) injecting sterilant vapor into the resistometer up to a sterilant vapor pressure to obtain an exposed one or more BIs;
   (d) repeating (a) to (c) one or more times to obtain one or more additional exposed one or more BIs, the sterilant vapor pressure being different for each exposure;
   (e) measuring a number of surviving microorganisms in each of the exposed one or more BIs to obtain a record of the number of surviving microorganisms for each sterilant vapor pressure used;
   (2) determining the resistance characteristics of the one or more BIs of the batch on the basis of the record;
   (3) identifying the one or more BIs as being suitable for the sterilization process on the basis of the resistance characteristics; and
   (4) informing a user of the sterilization process of the suitability of the one or more BIs so identified.

2. The method of claim 1, wherein injecting the sterilant vapor into the resistometer includes gradually injecting the sterilant vapor into the resistometer, wherein each sterilant vapor pressure has a different injection time, which is equal to the time required to inject the sterilant vapor in order to reach the sterilant vapor pressure of the respective exposed one or more BIs.

3. The method of claim 2, wherein the gradually injecting includes pulsed injection of the sterilant vapor for the generation of a layer of micro-condensation of the sterilant in the resistometer.

4. The method of claim 1, further comprising:
   (1.1) setting a temperature in the resistometer to a first temperature, prior to injecting the sterilant vapor into the resistometer, the record of the number of surviving microorganisms for each sterilant vapor pressure used to obtain the exposed one or more BIs being for the first temperature and constituting a first record;
   (1.2) repeating (1.1) with another one or more BIs at a second temperature, different from the first temperature, the record of the number of surviving microorganisms for each sterilant vapor pressure used to obtain the exposed one or more BIs at the second temperature constituting a second record;
   in accordance with the first record and the second record, determining the resistance characteristics of the one or more BIs for a third temperature different from the first temperature and the second temperature;
   identifying the one or more BIs as being suitable for the sterilization process at the third temperature on the basis of the resistance characteristics for the third temperature; and
   informing a user of the sterilization process of the suitability of the one or more BIs so identified for the third temperature.

5. The method of claim 1, further comprising the resistance characteristics of an unspent one or more BIs of the batch of BIs against a standard.

6. The method of claim 1, wherein the sterilant vapor is hydrogen peroxide vapor.

7. The method of claim 1, further comprising carrying out the sterilization process in a sterilizer system with the identified one or more BIs.

* * * * *